United States Patent
Tsuji et al.

(10) Patent No.: US 11,828,751 B2
(45) Date of Patent: Nov. 28, 2023

(54) METHOD FOR EVALUATING DRUG RESPONSIVENESS AND DRUG RESPONSIVENESS EVALUATION SYSTEM

(71) Applicant: Panasonic Intellectual Property Management Co., Ltd., Osaka (JP)

(72) Inventors: Kiyotaka Tsuji, Osaka (JP); Yumiko Kato, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 766 days.

(21) Appl. No.: 17/001,243

(22) Filed: Aug. 24, 2020

(65) Prior Publication Data
US 2020/0386743 A1 Dec. 10, 2020

Related U.S. Application Data

(63) Continuation of application No. PCT/JP2019/018853, filed on May 13, 2019.

(30) Foreign Application Priority Data

Jun. 13, 2018 (JP) .................... 2018-112485

(51) Int. Cl.
*C12Q 1/00* (2006.01)
*G01N 33/50* (2006.01)
*G01N 33/487* (2006.01)

(52) U.S. Cl.
CPC ... *G01N 33/5061* (2013.01); *G01N 33/48728* (2013.01); *G01N 2800/709* (2013.01)

(58) Field of Classification Search
CPC ................................................. G01N 33/5061
See application file for complete search history.

(56) References Cited

U.S. PATENT DOCUMENTS

| | | | |
|---|---|---|---|
| 2013/0230881 A1 | 9/2013 | Yasuda et al. | |
| 2015/0276708 A1 | 10/2015 | Kataoka et al. | |
| 2016/0011176 A1* | 1/2016 | Yasuda | G01N 15/1031 |
| | | | 435/402 |
| 2018/0251714 A1 | 9/2018 | Liu et al. | |

FOREIGN PATENT DOCUMENTS

| | | |
|---|---|---|
| WO | 2012/043820 | 4/2012 |
| WO | 2014/065329 | 5/2014 |
| WO | 2014/098182 | 6/2014 |
| WO | 2016/060260 | 4/2016 |

OTHER PUBLICATIONS

International Search Report of PCT application No. PCT/JP2019/018853 dated Jun. 25, 2019.

* cited by examiner

*Primary Examiner* — Albert M Navarro
(74) *Attorney, Agent, or Firm* — Wenderoth, Lind & Ponack, L.L.P.

(57) ABSTRACT

A method for evaluating drug responsiveness includes disposing a myocardial cell produced through differential induction onto a board including an electrode, administering a drug to the myocardial cell, continuously applying, after the drug is administered, a pulse current or a pulse voltage to the myocardial cell through the electrode for a certain period of time, measuring, after the certain period of time has elapsed, a pulsation characteristic of the myocardial cell, and evaluating responsiveness of the myocardial cell to the drug on a basis of the pulsation characteristic.

8 Claims, 11 Drawing Sheets

31 or 32 or 33

31 or 32 or 33

$FPDc = FPD/(ISI)^{1/3}$

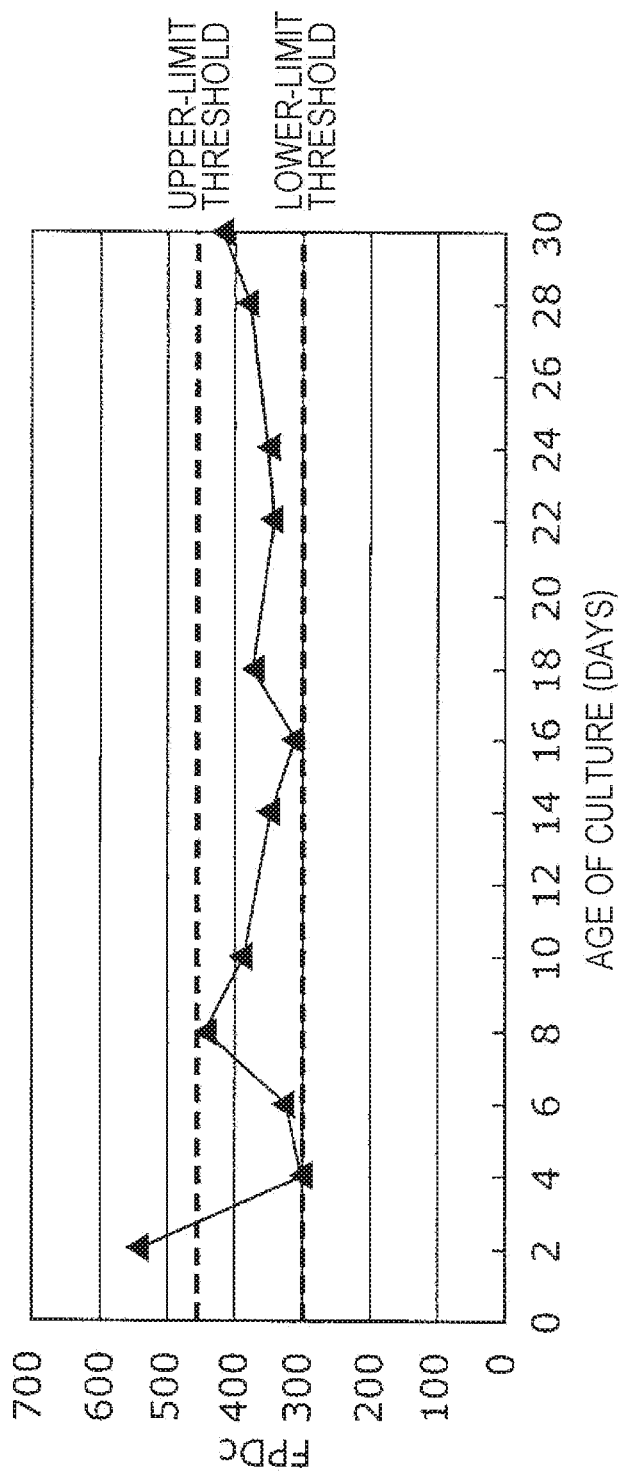

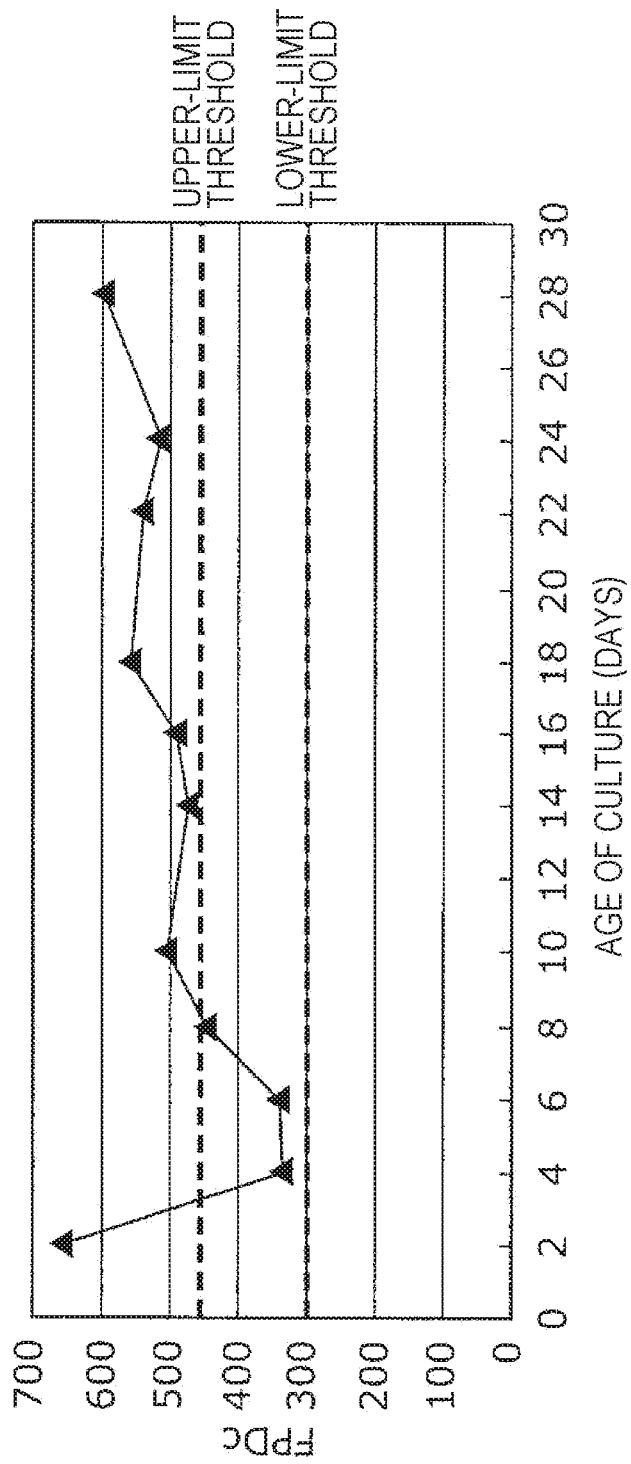

METHOD FOR EVALUATING DRUG RESPONSIVENESS AND DRUG RESPONSIVENESS EVALUATION SYSTEM

BACKGROUND

1. Technical Field

The present disclosure relates to a method for evaluating drug responsiveness and a drug responsiveness evaluation system used to evaluate responsiveness of myocardial cells to a drug.

2. Description of the Related Art

Cardiotoxicity of drugs is one of major reasons behind a ban on sales of the drugs. Techniques for accurately evaluating responsiveness of myocardial cells to drugs, therefore, are desired. In International Publication No. 2012/043820, for example, forced pulsatile stimulation is given to a myocardial cell population exposed to a flow of liquid containing a drug, and a degree of cardiotoxicity due to the drug is evaluated from a response to the stimulation.

SUMMARY

When myocardial cells produced through differential induction are cultured on a board including electrodes, however, it becomes, in a relatively short period of time, difficult to evaluate the myocardial cells. That is, even if a drug is not administered, it becomes difficult for the myocardial cells to maintain normal pulsation in a relatively short period of time. It is therefore difficult to evaluate long-term responsiveness of the myocardial cells to a drug and conduct a chronic cardiotoxicity test on a drug using the myocardial cells.

One non-limiting and exemplary embodiment provides a method for evaluating drug responsiveness and the like capable of evaluating long-term responsiveness of myocardial cells produced through differential induction to a drug.

In one general aspect, the techniques disclosed here feature a method for evaluating drug responsiveness. The method includes disposing a myocardial cell produced through differential induction onto a board including an electrode, administering a drug to the myocardial cell, continuously applying, after the drug is administered, a pulse current or a pulse voltage to the myocardial cell through the electrode for a certain period of time, measuring, after the certain period of time has elapsed, a pulsation characteristic of the myocardial cell, and evaluating responsiveness of the myocardial cell to the drug on a basis of the pulsation characteristic. The certain period of time is 30 days or longer.

According to the present disclosure, long-term responsiveness of myocardial cells produced through differential induction to a drug can be evaluated.

It should be noted that this general or specific aspect may be implemented as an apparatus, a system, an integrated circuit, a computer program, a computer-readable storage medium, or any selective combination thereof. The computer-readable storage medium is, for example, a nonvolatile storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 12A is a graph of corrected field potential duration (FPDc) in an example; and FIG. 12B is a graph of FPDc in a comparative example.

DETAILED DESCRIPTION

Figure 1:
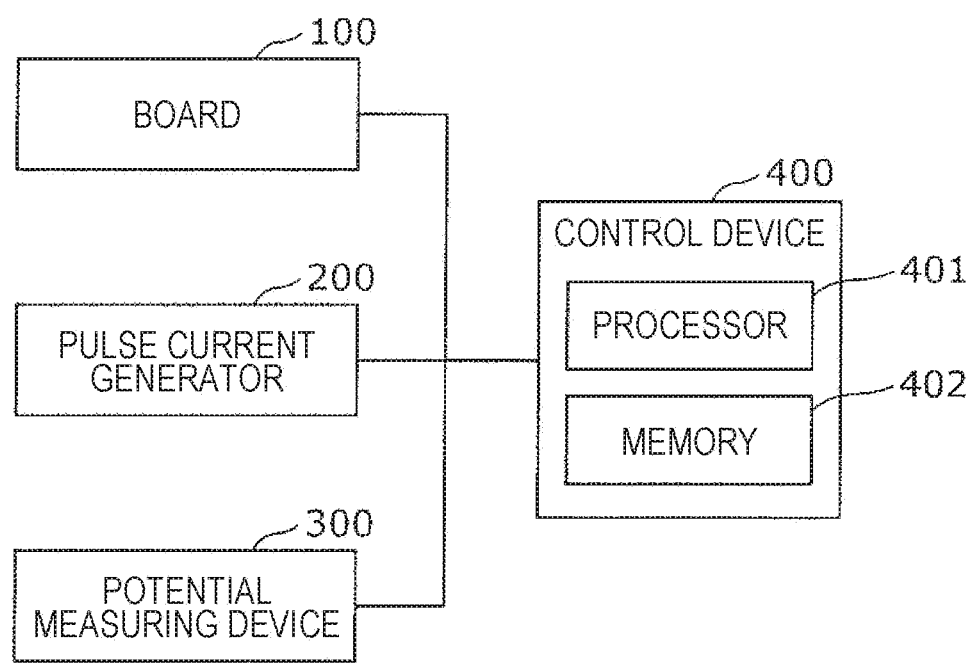
FIG. 1 is a block diagram illustrating the configuration of a drug responsiveness evaluation system according to a first embodiment.

Embodiments will be specifically described hereinafter with reference to the drawings.

The embodiments that will be described hereinafter are general or specific examples. Values, shapes, materials, components, arrangement positions and connection modes of the components, steps, order of the steps, and the like described in the following embodiments are examples, and do not limit the claims. Among the components described in the following embodiments, ones not described in the independent claims, which define broadest concepts, will be described as optional components. The drawings are not necessarily strict diagrams. In the drawings, substantially the same components are given the same reference numerals, and redundant description thereof is omitted or simplified.

First Embodiment

First, a first embodiment will be specifically described with reference to the drawings.

Configuration of Drug Responsiveness Evaluation System

First, the overall configuration of a drug responsiveness evaluation system will be described with reference to FIG. 1.

FIG. 1 is a block diagram illustrating the configuration of the drug responsiveness evaluation system according to the first embodiment. The drug responsiveness evaluation system includes a board 100, a pulse current generator 200, a potential measuring device 300, and a control device 400.

The board 100 includes electrodes on a surface thereof. Myocardial cells produced through differential induction are disposed on the surface of the board 100, and a drug is administered to the myocardial cells. The electrodes at least include first electrodes and measuring electrodes. A detailed configuration of the board 100 will be described later with reference to the drawings.

Myocardial cells exhibit the same characteristics as cardiac muscle cells. For example, myocardial cells are produced from pluripotent stem cells through differential induction.

Pluripotent stem cells have self-replicating ability and pluripotency. As the pluripotent stem cells, for example, embryonic stem (ES) cells or induced pluripotent stem (iPS) cells may be used. If pluripotent stem cells other than ES cells and iPS cells come into existence as a result of evolution of technologies for producing pluripotent stem cells or other derivative technologies, such pluripotent stem cells may be used, instead. The myocardial cells are not limited to cells produced from pluripotent stem cells through differential induction. For example, the myocardial cells may be produced from extracted in vivo cells (e.g., cardiac fibroblasts) through artificial differential induction. That is, the myocardial cells may be produced without using pluripotent stem cells.

The pulse current generator 200 is electrically connected to at least the first electrodes and generates a pulse current. As a result, the pulse current generator 200 applies the pulse current to the myocardial cells through the first electrodes.

The potential measuring device 300 is electrically connected to at least the measuring electrodes and measures temporal changes in extracellular potential caused by pulsation of the myocardial cells. More specifically, the potential measuring device 300 is an amplifier for measuring cellular potential, for example, and measures potential differences between the measuring electrodes and reference electrodes.

The control device 400 includes a processor 401 and a memory 402. The memory 402 stores, for example, an instruction or a software program. When the instruction or the software program is executed, the processor 401 performs the following. First, the processor 401 continuously applies a pulse current to myocardial cells administered with a drug through the pulse current generator 200 and the first electrode over a certain period of time. After the certain period of time elapses, the processor 401 measures a pulsation characteristic of the myocardial cells through the potential measuring device 300 and the measuring electrodes, The processor 401 then evaluates responsiveness of the myocardial cells to the drug after the certain period of time on the basis of the measured pulsation characteristic.

When a pulse current is continuously applied over a certain period of time, the pulse current is applied substantially at any time point in the certain period of time. The application of the pulse current, however, may be temporarily stopped in the certain period of time. That is, when a pulse current is continuously applied, the application may be stopped for a short period relative to the certain period of time.

As the certain period of time, for example, a period suitable for chronic toxicity test, that is, a relatively long period, is used. More specifically, the certain period of time may be, for example, 16 days or longer, or 30 days or longer.

Configuration of Board

Figure 2:
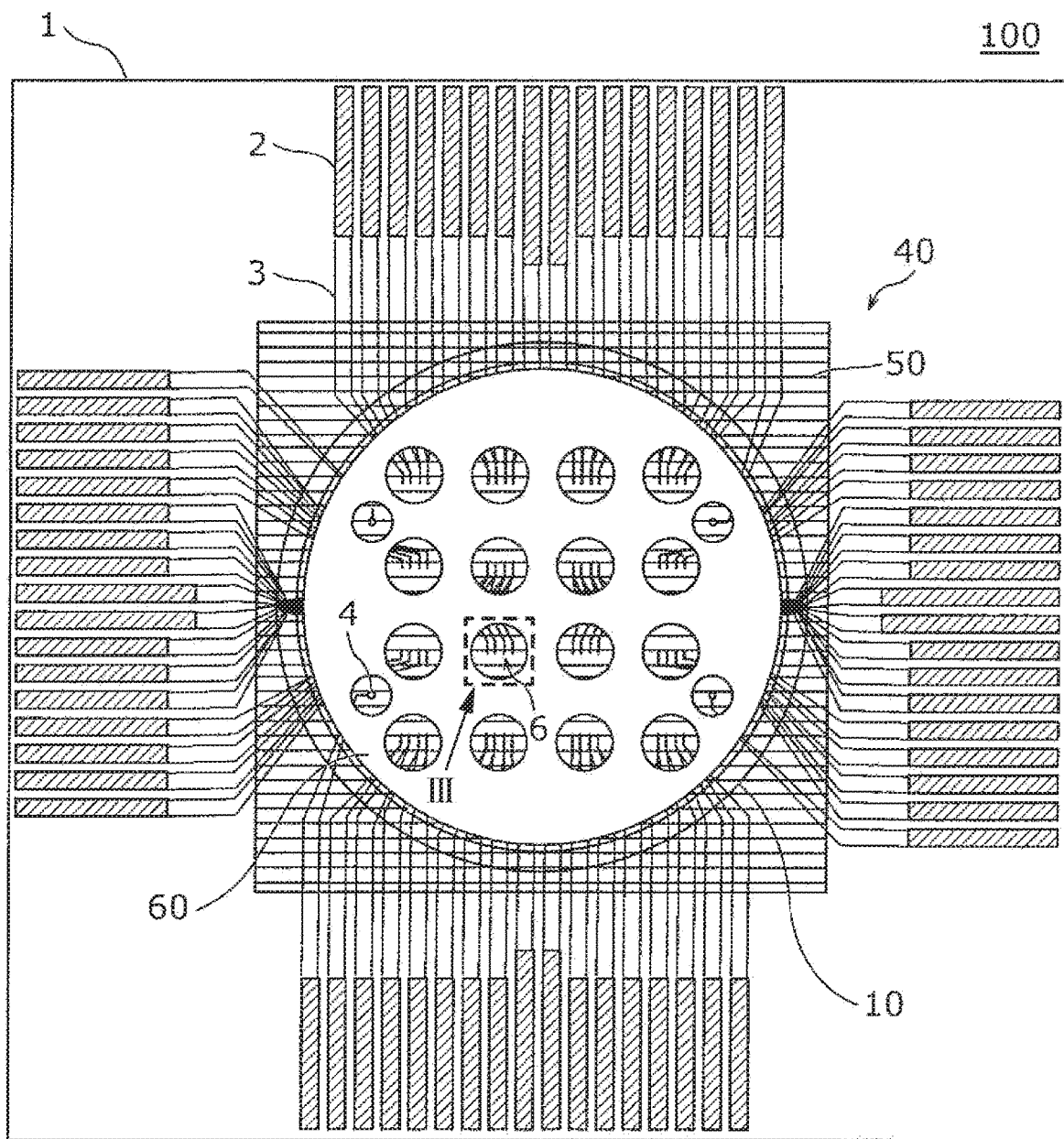
FIG. 2 is a plan view of a board according to the first embodiment.

Next, an example of the configuration of the board 100 according to the first embodiment will be specifically described with reference to FIGS. 2 to 5. FIG. 2 is a plan view of the board according to the first embodiment. As illustrated in FIG. 2, the board 100 includes a glass plate 1, wires 3, an enclosing member 10, an insulating film 40, and a silicone resin sheet 60.

The glass plate 1 is, for example, 0.7 mm in thickness and 50 mm×50 mm=2,500 mm$^2$ in area. The wires 3 are formed on a surface of the glass plate 1.

An electrical contact 2 is formed at one end of each of the wires 3, and an electrode is formed at another end. The wires 3 can be formed, for example, by etching an indium tin oxide film having a thickness of 150 nm using a photoresist.

In FIG. 2, the number of wires 3 is 68. That is, the board 100 includes 68 electrodes and 68 electrical contacts. The 68 electrodes include 16 electrode sets 6 and four reference electrodes 4. The 16 electrode sets 6 each include four electrodes. The number of electrode here is an example, and is not limited to this.

The insulating film 40 is composed of, for example, a photosensitive acrylic resin and covers the surface of the glass plate 1. The electrical contacts 2, the electrode sets 6, and the reference electrodes 4, however, are not covered by the insulating film 40.

The enclosing member 10 encloses an area including the electrode sets 6 and the reference electrodes 4. Here, the enclosing member 10 is a glass member having a shape of a circular wall. The enclosing member 10 has, for example, an inside diameter of 22 mm, an outside diameter of 25 mm, and a height of 10 mm.

The silicone resin sheet 60 covers the insulating film 40 within the area enclosed by the enclosing member 10. The silicone resin sheet 60, however, does not cover surrounding areas of the electrode sets 6 and the reference electrodes 4. The silicone resin sheet 60 separates the surrounding areas of the electrode sets 6 from one another. As a result, an effect of myocardial cells disposed in a surrounding area of an electrode set 6 upon myocardial cells disposed in the surrounding areas of the other electrode sets 6 can be suppressed. The silicone resin sheet 60 is about 1 mm in thickness, for example, and glued to the insulating film 40 with a silicone adhesive.

Figure 3:
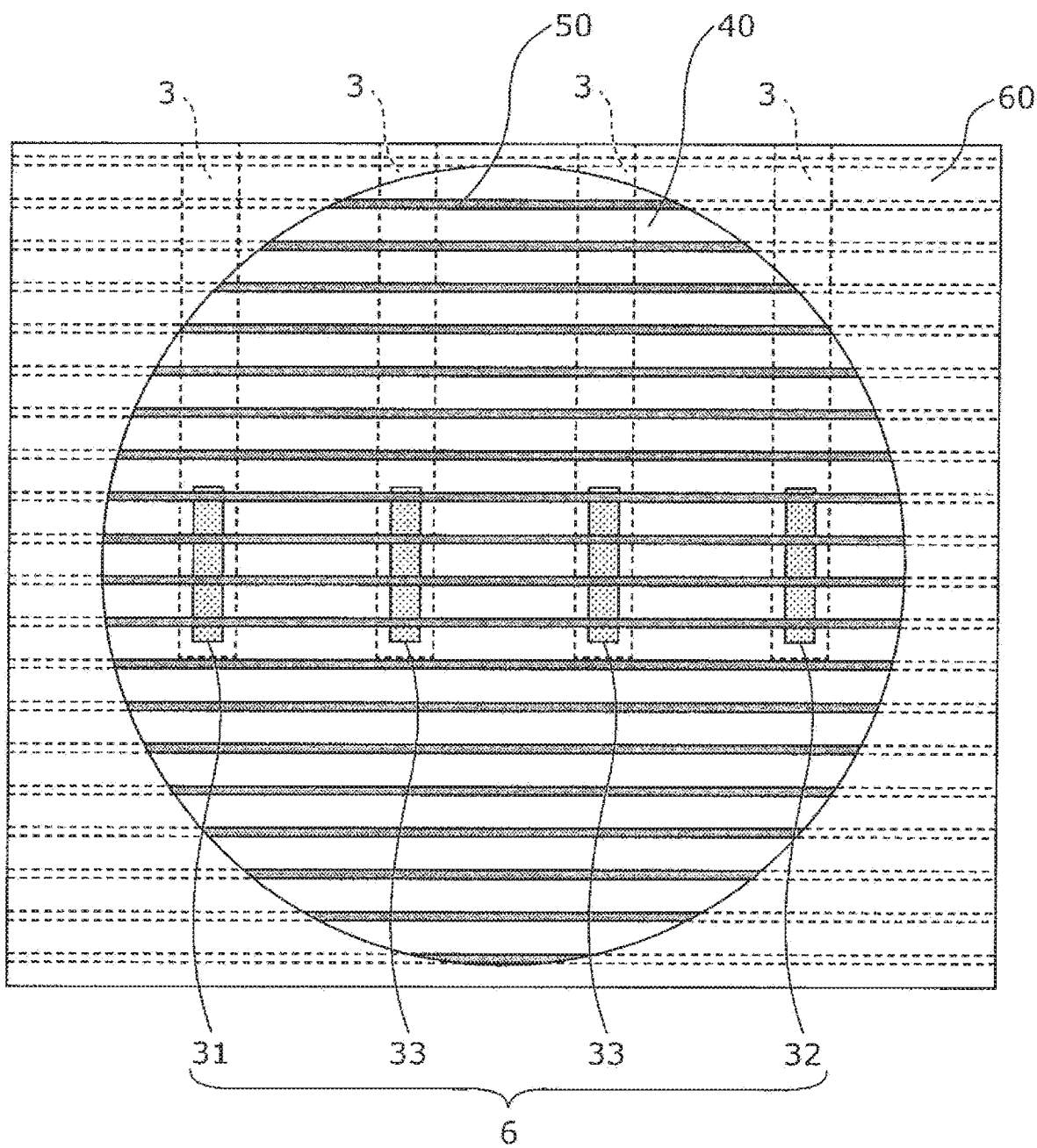
FIG. 3 is an enlarged plan view of the board according to the first embodiment.

Here, an electrode set 6 and a surrounding area thereof will be described with reference to FIG. 3. FIG. 3 is an enlarged plan view of the board according to the first embodiment. More specifically, FIG. 3 is an enlarged view of an area HI illustrated in FIG. 2.

As illustrated in FIG. 3, the surrounding area of the electrode set 6 is covered by the insulating film 40 but is not covered by the silicone resin sheet 60. The electrodes included in the electrode sets 6 are not covered by the insulating film 40. That is, the electrodes are exposed on the surface of the board 100.

The electrode set 6 includes a first electrode 31, a second electrode 32, and measuring electrodes 33. The first electrode 31 and the second electrode 32 are electrically connected to the pulse current generator 200 through the electrical contacts 2. The measuring electrodes 33 are electrically connected to the potential measuring device 300 through the electrical contacts 2.

Insulating fibers 50 extend over the insulating film 40 and the electrode set 6 in the same direction at certain intervals. In the present embodiment, the direction in which the insulating fibers 50 extend is a direction (a lateral direction in FIG. 3) parallel to a line connecting the first electrode 31 and the second electrode 32 when the board 100 is viewed from above. "Parallel" herein refers to not only strict parallelism but also substantial parallelism.

The insulating fibers 50 have cytocompatibility and is composed of, for example, polymethylglutarimide. The insulating fibers 50 can be provided on the insulating film 40 and the electrode sets 6 by, for example, applying aluminum tape on which nanofibers are formed through electrospinning to the insulating film 40 and the electrode sets 6 and then peeling off the aluminum tape.

Figure 4:
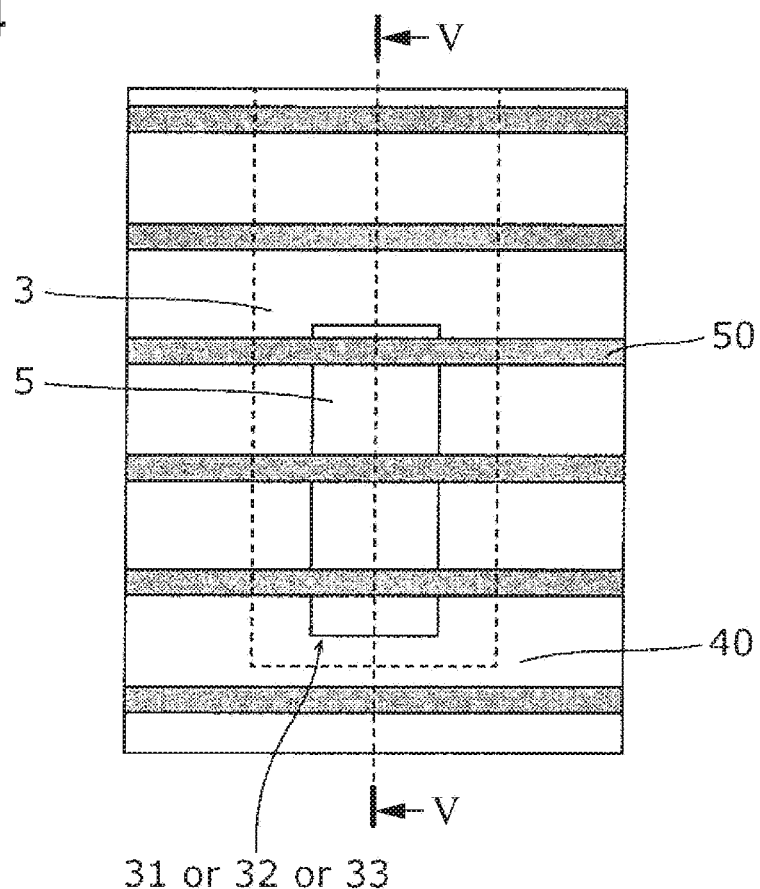
FIG. 4 is a plan view of a first electrode, a second electrode, or a measuring electrode according to the first embodiment.
Figure 5:
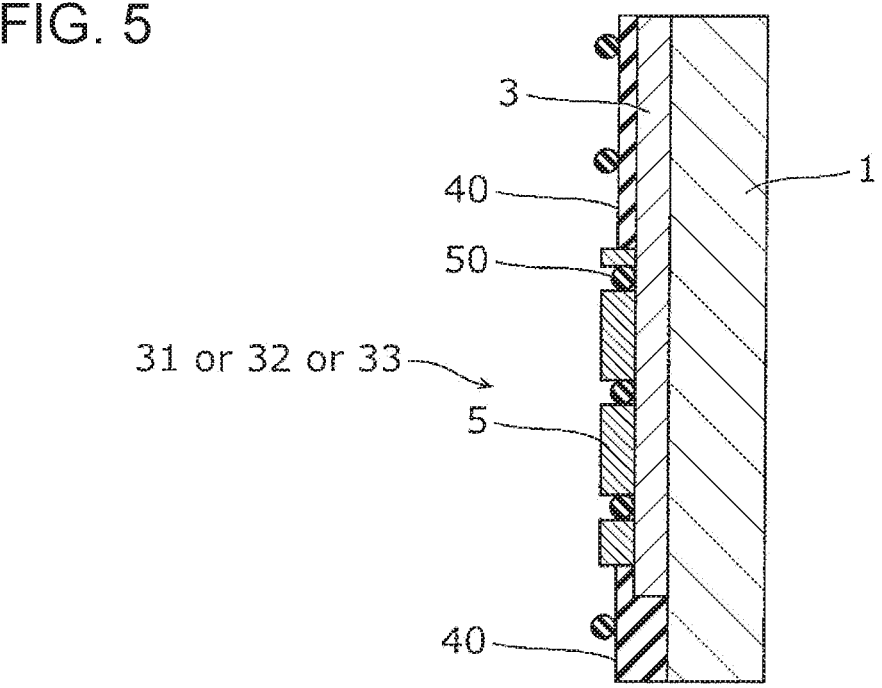
FIG. 5 is a cross-sectional view of the first electrode, the second electrode, or the measuring electrode according to the first embodiment.

Here, the structure of an electrode (the first electrode 31, the second electrode 32, or the measuring electrode 33) included in each electrode set 6 will be specifically described with reference to FIGS. 4 and 5. FIG. 4 is a plan view of the first electrode 31, the second electrode 32, or the measuring electrode 33 according to the first embodiment. FIG. 5 is a cross-sectional view of the first electrode 31, the second electrode 32, or the measuring electrode 33 according to the first embodiment. More specifically, FIG. 5 is a cross-sectional view taken along line v-v illustrated in FIG. 4.

The first electrode 31, the second electrode 32, or the measuring electrode 33 is a part of a wire 3 that is not covered by the insulating film 40. A surface of the first electrode 31, the second electrode 32, or the measuring electrode 33 is covered by insulating fibers 50 and platinum black 5. The platinum black 5 covers a part of the wire 3 that is not covered by the insulating film 40 or the insulating fibers 50. The part of the wire 3 covered by the platinum black 5 functions as an electrode.

The reference electrodes 4 each have the same structure as each of the electrodes included in the electrode sets 6 and are exposed on the surface of the board 100. The size of each of the reference electrodes 4 may be different from the size of each of the electrodes included in the electrode sets 6. The reference electrodes 4 are electrically connected to the potential measuring device 300.

Method for Evaluating Drug Responsiveness

Figure 6:
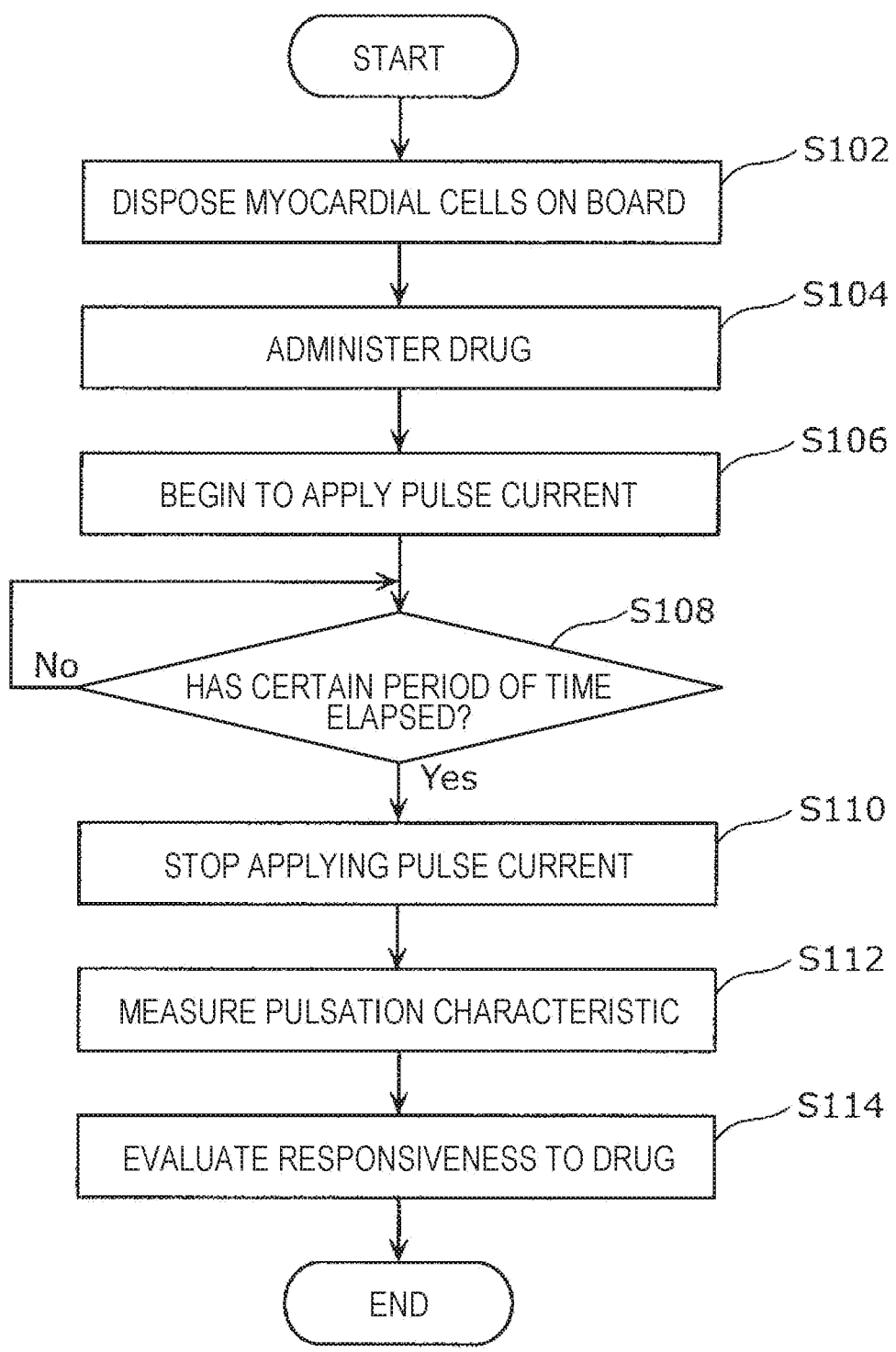
FIG. 6 is a flowchart illustrating a method for evaluating drug responsiveness according to the first embodiment.
Figure 7:
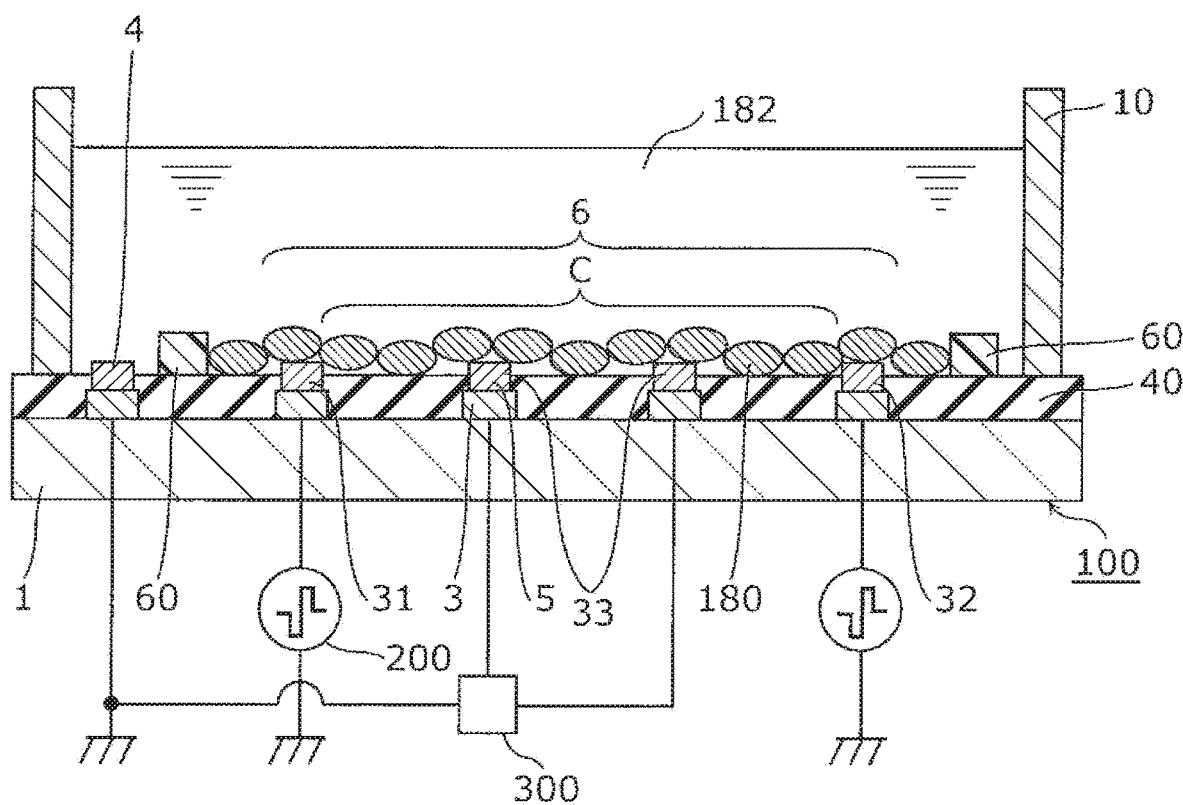
FIG. 7 is a cross-sectional view of the board on which myocardial cells are disposed according to the first embodiment.

A method for evaluating drug responsiveness using the board 100 will be specifically described with reference to FIGS. 6 to 9. FIG. 6 is a flowchart illustrating a method for evaluating drug responsiveness according to the first embodiment. FIG. 7 is a cross-sectional view of the board 100 on which myocardial cells 180 are disposed according to the first embodiment. FIG. 7 is a schematic diagram used for description, and does not strictly match the configuration illustrated in FIG. 2.

First, the myocardial cells 180 produced through differential induction are disposed on the board 100 (S102). For example, a liquid medium 182 containing the myocardial cells 180 is prepared and supplied onto the board 100 in an area surrounded by the enclosing member 10. As a result, the myocardial cells 180 are disposed on the board 100 as illustrated in FIG. 7.

Consequently, the surface of the first electrode 31, the surface of the second electrode 32, and an area C are covered by the myocardial cells 180. A surface of the reference electrode 4, on the other hand, is not covered by the myocardial cells 180. The reference electrodes 4 is in contact with the liquid medium 182 and keeps the potential of the liquid medium 182 at a reference potential (GNB).

Next, a drug is administered to the myocardial cells 180 (S104). That is, a drug is administered to the liquid medium 182 containing the myocardial cells 180. The responsiveness of the myocardial cells 180 to the administered drug is evaluated. That is, for example, the administered drug is a drug whose cardiotoxicity is to be evaluated.

Figure 8:
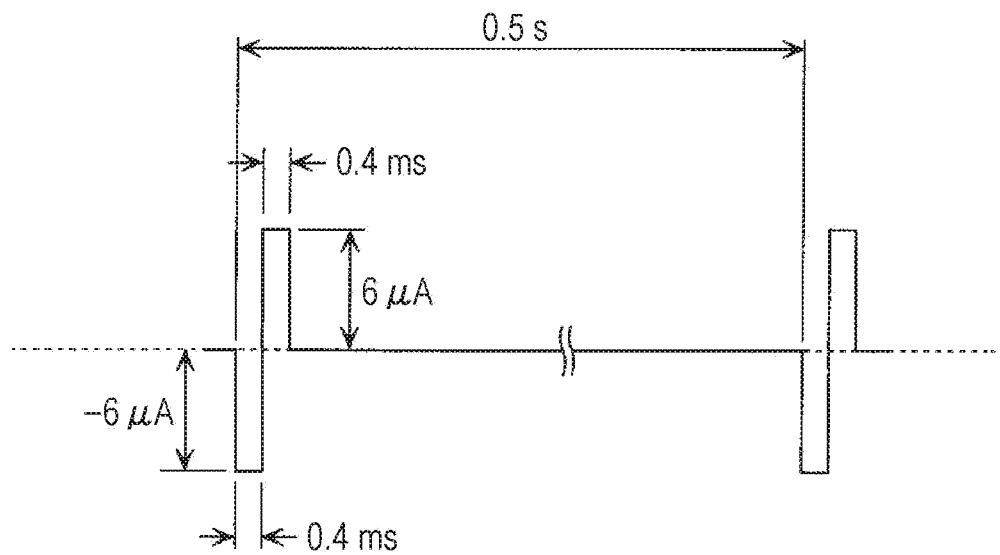
FIG. 8 is a graph illustrating an example of a pulse current according to the first embodiment.

Next, the processor 401 of the control device 400 generates a pulse current with the pulse current generator 200 and begins to apply the pulse current to the myocardial cells 180 (S106). The pulse current will be described with reference to FIG. 8. FIG. 8 is a graph illustrating an example of the pulse current according to the first embodiment.

The pulse current has a period of, say, 0.333 to 2 seconds (0.5 second in FIG. 8). Each pulse is either positive or negative. In FIG. 8, first, a negative pulse is applied, and then a positive pulse is applied without a gap. While the negative pulse is being applied, current flows from the myocardial cells 180 to the first electrode 31 or the second electrode 32. While the positive pulse is being applied, on the other hand, current flows from the first electrode 31 or the second electrode 32 to the myocardial cells 180.

In FIG. 8, for example, each pulse has a duration of 0.05 to 4 ms (0.4 ms in FIG. 8) and a height (i.e., a current value) of 1 to 20 µA (6 µA in FIG. 8). The amount of electric charge transported by each pulse (i.e., the area of each pulse in FIG. 8) is, for example, within a range of 0.1 to 1.0 nC. A ratio of the amount of electric charge transported by each pulse to the area of the first electrode 31 or the second electrode 32 is, for example, within a range of 0.04 to 0.4 C/m$^2$. The amount of electric charge transported by each negative pulse (i.e., the area of each negative pulse in FIG. 8) matches the amount of electric charge transported by each positive pulse (i.e., the area of each positive pulse in FIG. 8).

The processor 401 of the control device 400 determines whether a certain period of time has elapsed since the beginning of the application of the pulse current or the administration of the drug (S108). If the certain period of time has not elapsed (NO in S108), the processor 401 repeats step S108. If the certain period of time has elapsed (YES in S108), the processor 401 stops applying the pulse current to the myocardial cells 180 (S110). A pulse current is thus continuously applied to the myocardial cells 180 for a certain period of time after a drug is administered.

Next, the processor 401 of the control device 400 measures a pulsation characteristic of the myocardial cells 180 (S112). More specifically, the processor 401 measures temporal changes in extracellular potential caused by the pulsation of the myocardial cells 180 by causing the potential measuring device 300 to measure a potential difference between the measuring electrodes 33 and the reference electrode 4 for a certain period of time. The certain period of time is, for example, about 1 minute. The processor 401 calculates the pulsation characteristic on the basis of the temporal changes in extracellular potential measured in this manner.

The pulsation characteristic is, for example, corrected field potential duration (FPDc). The FPDc is field potential duration (FPD) corrected using an interspike interval (ISI) and serves as an index used to evaluate a state of myocardial cells. The ISI indicates a pulsation interval, and the FPD indicates a period for which myocardial cells remains contracted.

Figure 9:
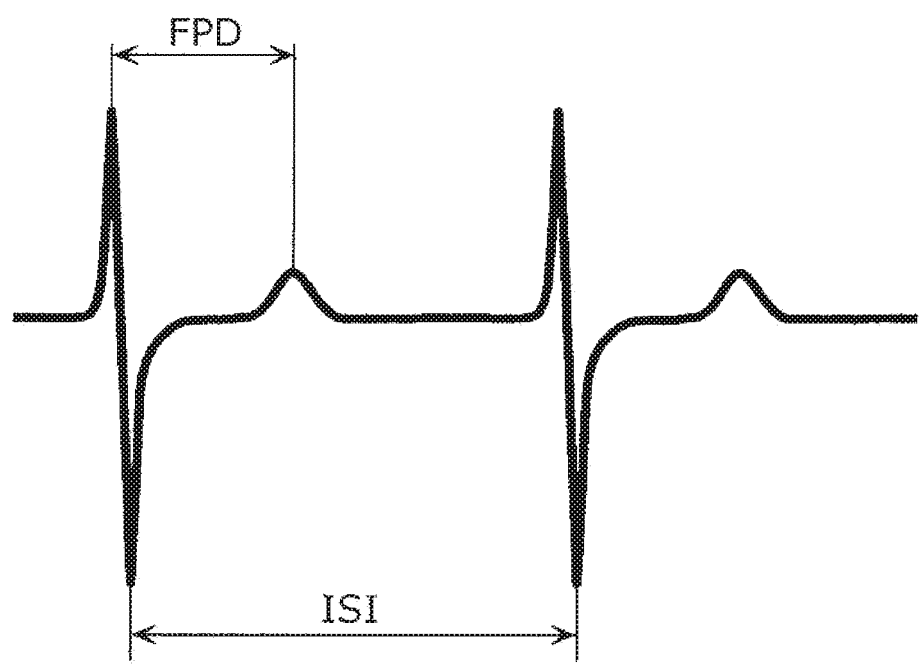
FIG. 9 is a graph illustrating a typical example of temporal changes in extracellular potential caused by pulsation of myocardial cells.

A relationship between the FPDc, the FPD, and the ISI will be described with reference to FIG. 9. FIG. 9 is a graph illustrating a typical example of temporal changes in extracellular potential caused by pulsation of myocardial cells. As illustrated in FIG. 9, the FPD and the ISI are both obtained from temporal changes in extracellular potential.

More specifically, the FPD is obtained from a time interval between a large peak and a small peak in temporal changes in extracellular potential. The ISI is obtained from a time interval between large peaks. The FPDc (ms) is calculated from the following expression using the FPD (ms) and the ISI (s) obtained from temporal changes in extracellular potential.

$$FPDc = FPD/(ISI)^{1/3}$$

Lastly, the processor 401 of the control device 400 evaluates the responsiveness of the myocardial cells 180 to the drug on the basis of the pulsation characteristic (S114). For example, the processor 401 evaluates the responsiveness of the myocardial cells 180 to the drug on the basis of FPDc of myocardial cells 180 to which no drug has been administered and the FPDc of the myocardial cells 180 to which the drug has been administered. More specifically, for example, the number of days for which the FPDc has remained between a lower-limit threshold and an upper-limit threshold (hereinafter referred to as "threshold days") is compared between the myocardial cells 180 to which no drug has been administered and the myocardial cells 180 to which the drug has been administered. If the threshold days of the myocardial cells 180 to which the drug has been administered are shorter than those of the myocardial cells 180 to which no drug has been administered by a certain value or larger, for example, it is determined that the drug has cardiotoxicity.

Advantageous Effects

As described above, with the drug responsiveness evaluation system and the method for evaluating drug responsiveness according to the present embodiment, a pulse current can be continuously applied to the myocardial cells 180 for a certain period of time through the first electrode 31 and the second electrode 32 after a drug is administered. Characteristics of the myocardial cells 180 stabilize for an extended period of time due to the pulse current. When the responsiveness of the myocardial cells 180 to the drug is evaluated after the certain period of time has elapsed since the administration of the drug, therefore, an effect of temporal deterioration of the characteristics of the myocardial cells 180 can be suppressed. Long-term responsiveness of the myocardial cells 180 to the drug, therefore, can be evaluated.

In addition, with the drug responsiveness evaluation system and the method for evaluating drug responsiveness according to the present embodiment, a period of 30 days or longer may be used as the certain period of time for which the pulse current is continuously applied to the myocardial cells 180. As a result, a period necessary to conduct a chronic cardiotoxicity test can be secured, and a chronic cardiotoxicity test can be conducted for a drug using the myocardial cells 180.

In addition, with the drug responsiveness evaluation system and the method for evaluating drug responsiveness according to the present embodiment, the board 100 includes the insulating fibers 50 extending in the same direction at the certain intervals. The myocardial cells 180, therefore, can be organized in the direction in which the insulating fibers 50 extend, which activates the pulsation of the myocardial cells 180. As a result, deterioration of the characteristics of the myocardial cells 180 can be suppressed compared to when the insulating fibers 50 are not provided, and longer-term responsiveness of the myocardial cells 180 to the drug can be evaluated.

Second Embodiment

Next, a second embodiment will be described. The present embodiment is different from the first embodiment mainly in that a pulse current is applied to myocardial cells even before a drug is administered and a pulsation characteristic is measured not only after a period in which the pulse current is continuously applied to the myocardial cells after the drug is administered but also during the period. The present embodiment will be specifically described hereinafter with reference to the drawings while focusing on differences from the first embodiment.

The configuration of a drug responsiveness evaluation system according to the present embodiment is substantially the same as that according to the first embodiment, and illustration and description thereof are omitted.

Method for Evaluating Drug Responsiveness

Figure 10:
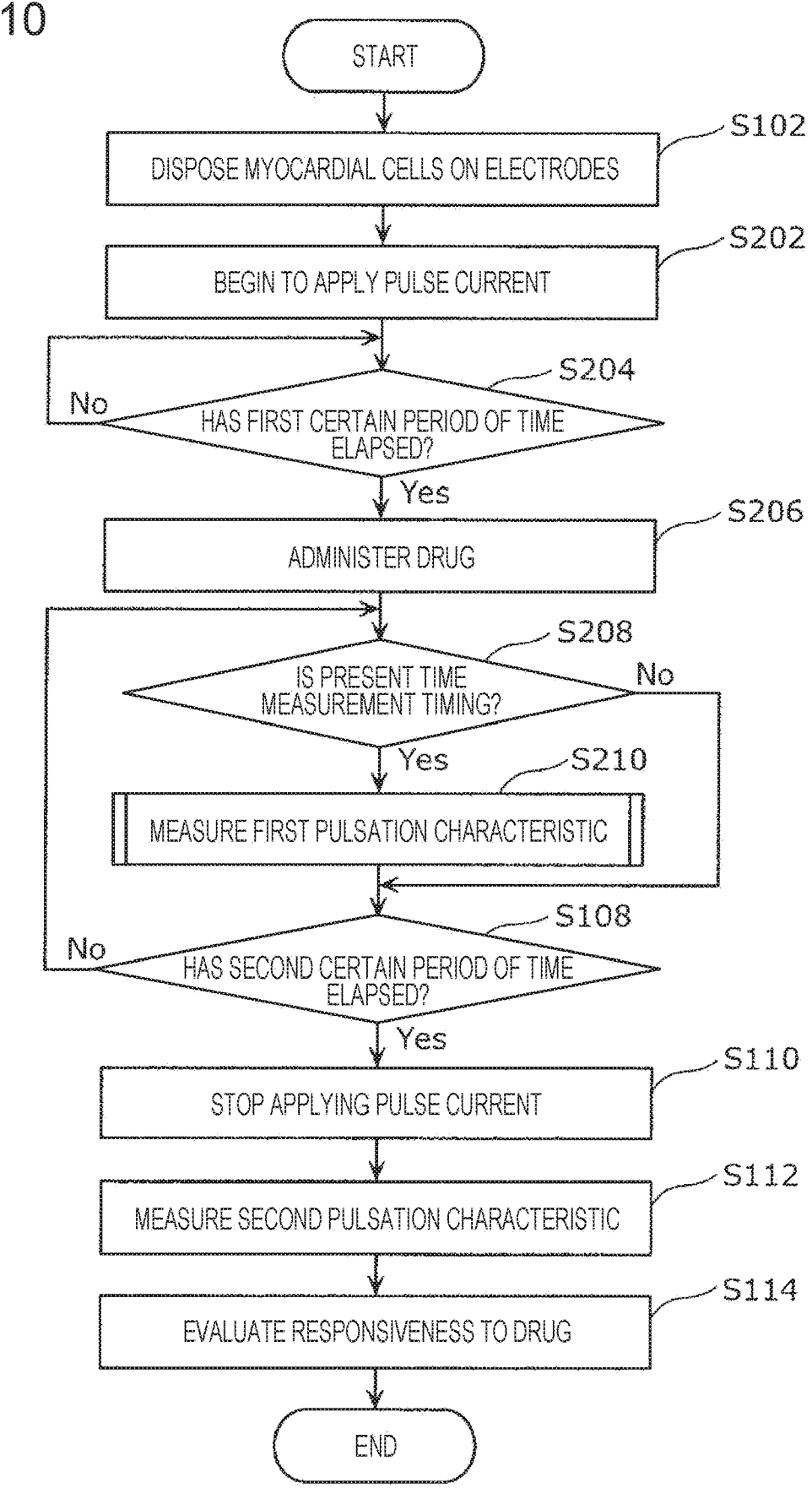
FIG. 10 is a flowchart illustrating a method for evaluating drug responsiveness according to a second embodiment.
Figure 11:
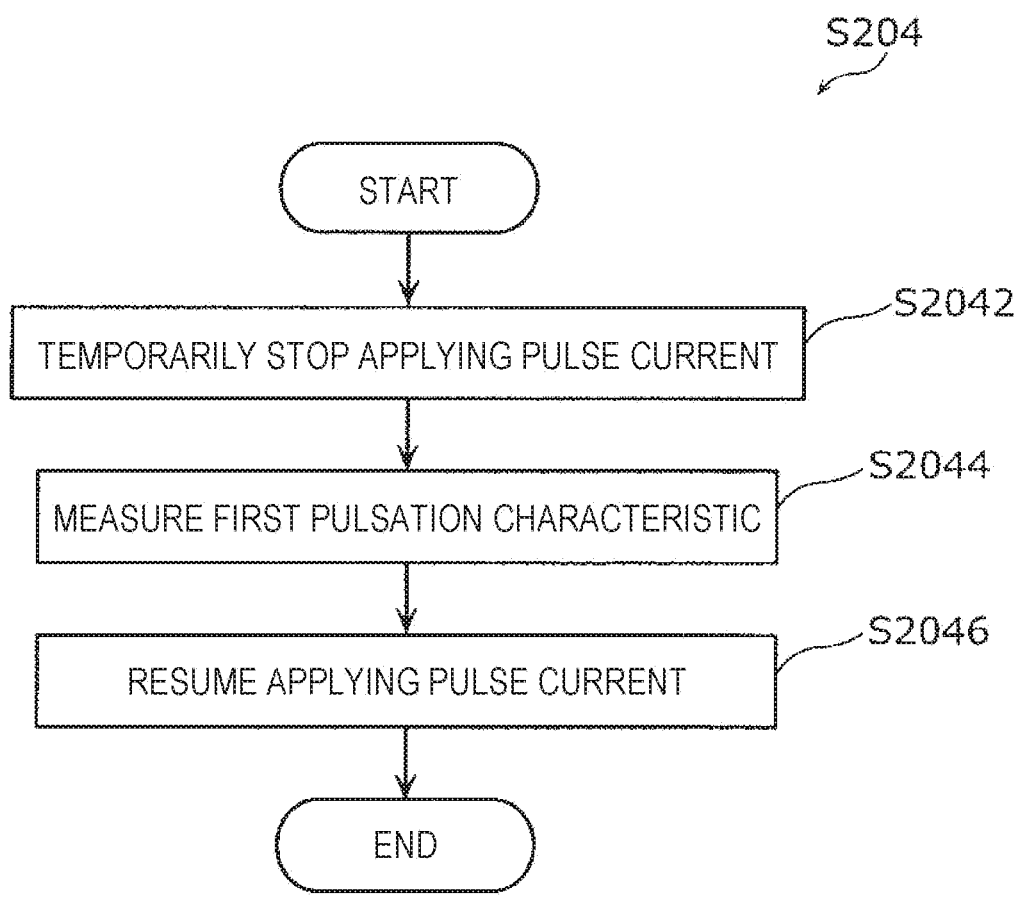
FIG. 11 is a flowchart illustrating a process for measuring a first pulsation characteristic according to the second embodiment.

A method for evaluating drug responsiveness will be specifically described with reference to FIGS. 10 and 11. FIG. 10 is a flowchart illustrating the method for evaluating drug responsiveness according to the second embodiment.

First, the myocardial cells 180 are disposed on the board 100 as in the first embodiment (S102). Next, the processor 401 of the control device 400 generates a pulse current with the pulse current generator 200 and begins to apply the pulse current to the myocardial cells 180 (S202). For example, the processor 401 begins to apply the pulse current four days after the myocardial cells 180 are disposed on the board 100 (on a fourth day of culture). As the pulse current, the pulse current illustrated in FIG. 8, for example, may be used.

The processor 401 of the control device 400 determines whether a first certain period of time has elapsed since the beginning of the application of the pulse current (S204). If the first certain period of time has not elapsed (NO in S204), the processor 401 repeats step S108. If the first certain period of time has elapsed (YES in S204), a drug is administered to the liquid medium 182 containing the myocardial cells 180 (S206). As a result, the pulse current is continuously applied to the myocardial cells 180 for the first certain period of time before the drug is administered.

The first certain period of time may be a period necessary for the myocardial cells 180 to mature. For example, the first certain period of time may be 10 to 14 days.

The processor 401 of the control device 400 determines whether the present time is a measurement timing (S208). If the present time is a certain time, for example, the processor 401 determines that the present time is a measurement timing. Alternatively, for example, if time elapsed since previous measurement of the pulsation characteristic (the administration of the drug if measurement has not been performed) is a certain period of time (e.g., 12, 24, or 48 hours), the processor 401 determines that the present time is a measurement timing.

Here, if the present time is a measurement timing (YES in S208), the processor 401 measures a first pulsation characteristic of the myocardial cells 180 (S210). Details of the measurement of the first pulsation characteristic will be described later with reference to FIG. 11. The processor 401 then determines whether a second certain period of time has elapsed since the drug is administered (S108). If the present time is not a measurement timing (NO in S208), on the other hand, the processor 401 skips the measurement of the first pulsation characteristic and determines whether the second certain period of time has elapsed since the drug is administered (S108).

Here, if the second certain period of time has not elapsed (NO in S108), the process returns to step S208. As a result, the first pulsation characteristic of the myocardial cells 180 is repeatedly measured at certain time intervals in the second certain period of time. If the second certain period of time has elapsed (YES in S108), on the other hand, the processor 401 stops applying the pulse current to the myocardial cells 180 (S110). The pulse current is thus continuously applied to the myocardial cells 180 for the second certain period of time after the drug is administered.

Next, the processor 401 of the control device 400 measures a second pulsation characteristic of the myocardial cells 180 (S112). The processor 401 then evaluates the responsiveness of the myocardial cells 180 to the drug on the basis of the first and second pulsation characteristics (S114).

Process for Measuring First Pulsation Characteristic

A process for measuring the first pulsation characteristic will be specifically described with reference to FIG. 11. FIG. 11 is a flowchart illustrating the process for measuring the first pulsation characteristic according to the second embodiment.

First, the processor 401 of the control device 400 temporarily stops applying the pulse current (S2042). The processor 401 then measures the first pulsation characteristic of the myocardial cells 180 (S2044). For example, after stopping applying the pulse current and waiting for a period of time long enough for spontaneous pulsation of the myocardial cells 180 to stabilize, the processor 401 measures the first pulsation characteristic. The period of time long enough for the spontaneous pulsation of the myocardial cells 180 to stabilize may be, for example, about 10 minutes.

The processor 401 of the control device 400 then resumes the application of the pulse current (S2043). The application of the pulse current is thus temporarily stopped for a relatively short period of time (e.g., about 11 minutes) in order to measure the first pulsation characteristic, and the application of the pulse current resumes (S2046).

Advantageous Effects

As described above, with the drug responsiveness evaluation system and the method for evaluating drug responsiveness according to the first embodiment, the first pulsation characteristic of the myocardial cells 180 can be measured in the second certain period of time. The progress of the pulsation characteristic of the myocardial cells 180 until the second certain period of time has elapsed since the administration of the drug, therefore, can be obtained, and the responsiveness of the myocardial cells 180 to the drug can be evaluated more accurately.

In addition, with the drug responsiveness evaluation system and the method for evaluating drug responsiveness according to the present embodiment, the application of the pulse current can be temporarily stopped in the measurement of the first pulsation characteristic. An effect of the pulse current upon the first pulsation characteristic, therefore, can be suppressed, and spontaneous pulsation characteristics of the myocardial cells 180 can be measured.

In addition, with the drug responsiveness evaluation system and the method for evaluating drug responsiveness according to the present embodiment, the pulse current can be continuously applied to the myocardial cells 180 for the first certain period of time before the drug is administered. As a result, maturation of the myocardial cells 180 can be facilitated, and the responsiveness of the myocardial cells 180 having characteristics closer to those of cardiac muscle cells to the drug can be evaluated.

EXAMPLE

Next, an example in which a pulse current was applied to myocardial cells using a board according to the above embodiments will be described. In this example, a pulse current was applied to myocardial cells without administering a drug. First, experiment conditions will be described.

In this example, myocardial cells differentiated from human iPS cells were used. As a liquid medium, a liquid medium suitable for myocardial cells (a liquid medium adjusted in accordance with a protocol described in an explanatory note provided by a seller of the myocardial cells) was used. The density of the myocardial cells on the board was $1.5 \times 10^4$ cells $\mu m^2$.

As a board, one obtained by removing the insulating fibers 50 from the board 100 described in the first embodiment was used. More specifically, the size of first electrodes, second electrodes, and measuring electrodes was 15 $\mu m \times 170$ $\mu m$. A distance between two adjacent electrodes included in each electrode set was 4 mm. The area of reference electrodes was 200 $\mu m^2$.

The pulse current illustrated in FIG. 8 was used. The pulse current was applied to the myocardial cells from a fourth day to 30th day of culture except when the liquid medium was replaced.

Temporal changes in extracellular potential caused by pulsation of the myocardial cells were measured by measuring a potential difference between the reference electrodes and the measuring electrodes for one minute at intervals of one day. The application of the pulse current was temporarily stopped for 10 minutes before the measurement of temporal changes in extracellular potential.

FPDc in this example was obtained from the temporal changes in extracellular potential measured in this manner. FIG. 12A is a graph of the FPDc in this example. FIG. 12B is a graph of FPDc in a comparative example. In the comparative example, a pulse current was not applied. Conditions other than the pulse current were the same between the example and the comparative example.

A lower-limit threshold and an upper-limit threshold illustrated in FIGS. 12A and 12B indicate a range of FPDc of myocardial cells available in evaluation of drug responsiveness. Here, 300 ms and 450 ms were used as the lower-limit threshold and the upper-limit threshold, respectively.

As can be seen from FIG. 12A, the FPDc in this example remained in the range of 300 ms to 450 ms from the fourth day to the 30th day of culture. As can be seen from FIG. 12B, on the other hand, the FPDc in the comparative example increased over time and exceeded 450 ms on the 10th day of culture.

By culturing the myocardial cells while stimulating the myocardial cells with the pulse current, an increase in FPDc of the myocardial cells over time could be suppressed, and characteristics of the myocardial cells could be stabilized for an extended period of time (30 days or longer).

Other Embodiments

Although the drug responsiveness evaluation system and the method for evaluating drug responsiveness according to one or more aspects of the present disclosure have been described on the basis of the above embodiments, the present disclosure is not limited to these embodiments. The one or more aspects of the present disclosure may also include modes obtained by modifying one of the above embodiments and modes constructed by combining together components in different embodiments, insofar as the scope of the present disclosure is not deviated from.

For example, although the insulating fibers 50 extending in the same direction are provided on the surface of the board 100 in the above embodiments, the arrangement mode of the insulating fibers 50 is not limited to this. For example, a direction in which insulating fibers extend may be different from that in which the insulating fibers 50 extend in the above embodiments. Alternatively, the board 100 need not include the insulating fibers 50. In this case, too, the characteristics of the myocardial cells 180 can be stabilized by a pulse current, and long-term responsiveness of the myocardial cells 180 to a drug can be evaluated. In addition, although there is no description of replacement of the liquid medium 182 in the above embodiments, the liquid medium 182 may be replaced at certain time intervals (e.g., every second day). In this case, a drug is administered to the liquid medium immediately after the replacement to maintain the concentration of the drug before and after the replacement of the liquid medium.

In addition, although FPDc is used as a pulsation characteristic in the above embodiments, the pulsation characteristic is not limited to this. For example, FPD or another feature value may be used as the pulsation characteristic, instead.

In addition, although the pulse current illustrated in FIG. 8 is used in the above embodiments, the pulse current used is not limited to this. For example, a period of the pulse current, pulse width, pulse height, or any selective combination thereof may be adjusted in accordance with the myocardial cells 180. In addition, a pulse voltage may be used instead of a pulse current. In this case, a pulse voltage generator is used instead of a pulse current generator.

In addition, although the reference electrodes 4 are provided on the surface of the board 100 in the above embodiments, an arrangement mode of the reference electrodes 4 is not limited to this. For example, the reference electrodes 4 may be provided on the enclosing member 10 in such a way as to come into contact with the liquid medium 182 supplied to the area inside the enclosing member 10.

In addition, the following embodiments are also included in the method for evaluating drug responsiveness in the present disclosure.

A method for evaluating drug responsiveness includes
 a step of obtaining a pulsation characteristic of a myocardial cell produced through differential induction, and
 a step of evaluating responsiveness of the myocardial cell to a drug on the basis of the pulsation characteristic,
 in which the pulsation characteristic is measured by administering the drug to the myocardial cell disposed on a board including an electrode, and
 continuously applying, after the drug is administered, a pulse current or a pulse voltage to the myocardial cell through the electrode for a certain period of time.

The method for evaluating drug responsiveness including the step of obtaining and the step of evaluating can be executed by a server apparatus. For example, the server apparatus and a terminal apparatus may be connected to each other by a network. The server apparatus may be configured to perform a process for evaluating information regarding a pulsation characteristic input from the terminal apparatus and output a result of the evaluation to the terminal apparatus.

The present disclosure can be used for an apparatus that examines chronic cardiotoxicity of drugs.

What is claimed is:

1. A method for evaluating drug responsiveness, the method comprising:
   disposing a myocardial cell produced through differential induction onto a board including an electrode;
   administering a drug to the myocardial cell;
   continuously applying, after the drug is administered, a pulse current or a pulse voltage to the myocardial cell through the electrode for a certain period of time;
   measuring, after the certain period of time has elapsed, a pulsation characteristic of the myocardial cell; and
   evaluating responsiveness of the myocardial cell to the drug on a basis of the pulsation characteristic,
   wherein the certain period of time is 30 days or longer.

2. The method according to claim 1,
   wherein the pulsation characteristic is corrected field potential duration.

3. The method according to claim 1,
   wherein the pulsation characteristic is a second pulsation characteristic,
   the method further comprising:
   measuring a first pulsation characteristic of the myocardial cell in the certain period of time; and
   evaluating the responsiveness of the myocardial cell of the drug on a basis of the first and second pulsation characteristics.

4. The method according to claim 3,
   wherein, in the measuring the first pulsation characteristic, the application of the pulse current or the pulse voltage is temporarily stopped.

5. The method according to claim 1,
   wherein the certain period of time is a second certain period of time,
   the method further comprising:
   continuously applying, before the drug is administered, a pulse current or a pulse voltage to the myocardial cell through the electrode for a first certain period of time.

6. The method according to claim 1,
   wherein the myocardial cell is a cell produced from a pluripotent stem cell through differential induction.

7. A drug responsiveness evaluation system comprising:
   a board including, on a surface of the board, electrodes including a first electrode and a measuring electrode, a myocardial cell produced through differential induction and administered with a drug being disposed on the surface of the board;
   a pulse current generator or a pulse voltage generator electrically connected to the first electrode;
   a potential measuring device electrically connected to the measuring electrode; and
   a control device including a processor and a memory,
   wherein, using the memory, the processor
   continuously applies a pulse current or a pulse voltage to the myocardial cell administered with the drug through the pulse current generator or the pulse voltage generator and the first electrode for a certain period of time,
   measures, after the certain period of time has elapsed, a pulsation characteristic of the myocardial cell through the potential measuring device and the measuring electrode, and
   evaluates responsiveness of the myocardial cell to the drug on a basis of the measured pulsation characteristic,
   wherein the certain period of time is 30 days or longer.

8. The drug responsiveness evaluation system according to claim 7,
   wherein the board includes, on the surface of the board, insulating fibers extending in a same direction at certain intervals.

* * * * *